Figure 1A:
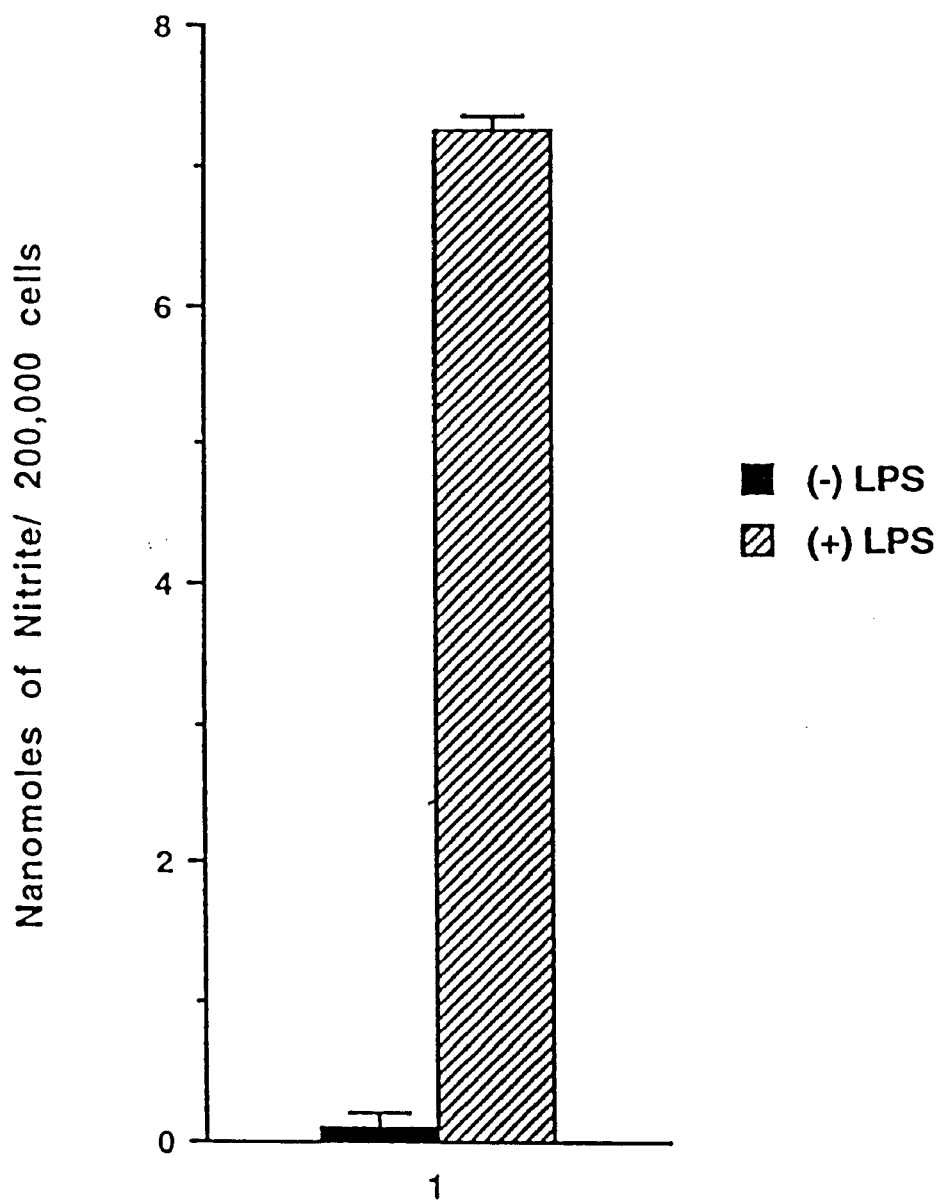

US006160021A

United States Patent [19]
Lerner et al.

[11] Patent Number: 6,160,021
[45] Date of Patent: Dec. 12, 2000

[54] METHOD FOR TREATING EPIDERMAL OR DERMAL CONDITIONS

[75] Inventors: Ethan A. Lerner, Newton; Abrar A. Qureshi, Brookline; Lisa H. Lerner, Newton, all of Mass.

[73] Assignee: The General Hospital Corporation, Boston, Mass.

[21] Appl. No.: 09/018,080

[22] Filed: Feb. 3, 1998

Related U.S. Application Data

[60] Provisional application No. 60/037,098, Feb. 4, 1997.

[51] Int. Cl.[7] .................. A61K 31/13; A61K 31/155; A61K 38/00; A61K 31/21
[52] U.S. Cl. .................. 514/645; 514/509; 514/634; 514/20
[58] Field of Search .................. 514/546, 634, 514/364, 398, 305, 599, 632, 152, 562, 509, 645

[56] References Cited

U.S. PATENT DOCUMENTS

| | | | |
|---|---|---|---|
| 5,227,459 | 7/1993 | Pawelek et al. | 528/206 |
| 5,352,440 | 10/1994 | Gilchrest et al. | 424/59 |
| 5,358,969 | 10/1994 | Williamson et al. | 514/632 |
| 5,449,688 | 9/1995 | Wahl et al. | 514/546 |
| 5,554,638 | 9/1996 | Dewhirst et al. . | |
| 5,599,984 | 2/1997 | Bianchi et al. | 564/157 |
| 5,674,907 | 10/1997 | Southan et al. | 514/634 |
| 5,710,181 | 1/1998 | Williamson et al. | 514/634 |
| 5,750,549 | 5/1998 | Caldwell et al. | 514/364 |
| 5,789,395 | 8/1998 | Amin et al. | 514/152 |
| 5,837,738 | 11/1998 | Williamson et al. | 514/634 |
| 5,847,004 | 12/1998 | Lai | 514/599 |
| 5,869,499 | 2/1999 | Satake et al. | 514/305 |
| 5,889,056 | 3/1999 | Hodson et al. | 514/562 |

FOREIGN PATENT DOCUMENTS

| | | | |
|---|---|---|---|
| WO 95/03810 | 2/1995 | WIPO . | |
| 98/11882 | 3/1998 | WIPO | A61K 31/045 |

OTHER PUBLICATIONS

Bredt et al. "Nitric Oxide, a Novel Neuronal Messenger," Neuron 8:3–11 (1992).

Chang et al., "B7–1 expression of Langerhans cells is up–regulated by proinflammatory cytokines, and is down–regulated by interferon–γ or by interleukin–10," Eur J Immunol 25:394–398 (1995).

Cui et al., "Activated Murine Macrophages Induce Apoptosis in Tumor Cells through Nitric Oxide–dependent or – independent Mechanisms," Cancer Res 54:2462–67 (1994).

Garthwaite, J. "Glutamate, nitric oxide and cell–cell signalling in the nervous system," Trends Neurosci 14: 60–67 (1991).

Huang et al., "Hypertension in mice lacking the gene for endothelial nitric oxide synthase," Nature 377:239–42 (1995).

Janssens et al., "Cloning and Expression of a cDNA Encoding Human Endothelium–derived Relaxing Factor/Nitric Oxide Synthase," J Biol Chem 267:14519–22 (1992).

Klostergaard, J., "Macrophage tumoricidal mechanisms," Res Immunol 144(4):274–76 (1993).

Liew et al., "Macrophage Killing of Leishmania Parasite in Vivo is Mediated by Nitric Oxide from L–Arginine," J. Immunol 144:4794–97 (1990).

Lyons et al., "Molecular Cloning and Functional Expression of an Inducible Nitric Oxide Synthase from a Murine Macrophage Cell Line," J Bio Chem 267:6370–74 (1992).

Moncada et al., "The L–Arginine–Nitric Oxide Pathway," New Eng J Med 329:2002–12 (1993).

Morita et al., "Clinical Application of Nitric Oxide Synthase Inhibitor for Atopic Dermatitis," Internat J Dermatol 34:294 (1995).

Ohshima et al., "Chronic infections and inflammatory processes as cancer risk factors: possible role of nitric oxide in carcinogenesis," Mutation Research 305:253–64 (1994).

Pollock et al., "Purification and characterization of particulate endothelium–derived relaxing factor synthase from cultured and native bovine aortic endothelial cells," Proc Natl Acad Sci USA 88:10480–84 (1991).

Ralevic et al., "Nitric oxide and sensory nerves are involved in the vasodilator response to acetylcholine but not calcitonin gene–related peptide in rat skin microvasculature," Br J Pharmacology 106:650–655 (1992).

Saenz et al., "Impaired Neurogenic and Endothelium–Mediated Relaxation of Penile Smooth Muscle From Diabetic Men with Impotence," New Eng J Med 320:1025–30 (1989).

Schmidt et al., "Purification and characterization of a human NO synthase," Biochem Biophys Res Comm 181:1372–77 (1991).

Snyder et al., "Biological Roles of Nitric Oxide," Sci Amer 5:68–77 (1992).

Stuehr et al., "Mammalian nitrate biosynthesis: Mouse macrophages produce nitrite and nitrate in response to *Escherichia coli* lipopolysaccharide," Proc Natl Acad Sci USA 82:7738–42, 1982.

Vane et al., "Regulatory Functions of the Vascular Endothelium," New Eng J Med 323:27–36 (1990).

Warren, J.B., "Nitric oxide and human skin blood flow responses to acetylcholine and ultraviolet light," The FASEB Journal 8:247–51 (1994).

Xie et al., "Cloning and Characterization of Inducible Nitric Oxide Synthase from Mouse Macrophages," Science 256:225–28 (1992).

Qureshi et al. "From bedside to the bench and back: nitric oxide and the cutis" abstract to Archives of Dermatology 132/8, pp. 889–900 (1996) Database EMBASE on STN, No. 96245989.

Bruch–Gerharz et al., "Nitric oxide in human skin: current status and future prospects" abstract to J. Invest. Dermatol., 110(1):1–7 (1998) Database CAPLUS on STN, No. 1998:37621.

(List continued on next page.)

Primary Examiner—William R. A. Jarvis
Assistant Examiner—Vickie Kim
Attorney, Agent, or Firm—Fish & Richardson P.C.

[57] ABSTRACT

A method of treating a subject for an unwanted epidermal or dermal condition comprising administering to the subject, a treatment which modulates the level of nitric oxide (NO) in the skin.

8 Claims, 5 Drawing Sheets

OTHER PUBLICATIONS

Benrath et al., Substance P and nitric oxide mediate wound healing . . . , Neurosci. Let., vol. 200(1) p. 17–20, 1995.

Romero–Graillet et al., Ultraviolet B radiation acts through . . . , Journal Of Biological Chemistry, vol. 271(45) p. 28052–28056, 1996.

Dr. V.B. Morhenn et al., Effect of nitroglycerin ointment . . . , Journal Of Cutaneous Med. & Surgery, vol. 2(2) p. 66–71, 1997.

Troman et al. "NO as a regulator of Keratinocyte proliferation", J. of Investigative Dermatology, vol. 103/3, p. 437, (Sep. 1994).

Sakai, M. et al., "Immunohistochemical localization of NO synthases in normal skin and psoriatic skin", Arch. Dermatol. Res. vol. 288/10. pp. 625–627, (1996).

METHOD FOR TREATING EPIDERMAL OR DERMAL CONDITIONS

This application is a continuation-in-part of U.S. provisional patent application Ser. No. 60/037,098, filed Feb. 4, 1997.

This invention was made with government support from the National Institutes of Health. Accordingly, the government has certain rights in the invention.

BACKGROUND OF THE INVENTION

The invention relates to modulation of nitric oxide (NO) to treat epidermal and dermal conditions.

Organic nitrates and their gaseous metabolic end-product, nitric oxide (NO), have been implicated to date in a vast array of biologically diverse activities (Snyder et al. (1992) *Sci Amer* 5:68–77). The growth in interest in the biological effects of NO began in 1980 when it was noticed that relaxation of blood vessels (vasodilatation) no longer occurred when the endothelial layer was stripped from the vessels. The molecule mediating this effect was termed endothelial-derived-relaxing-factor (EDRF). In 1987, EDRF was shown to be nitric oxide (NO).

Three nitric oxide synthase (NOS) isoforms have been characterized. A constitutive form is found in neuronal cells (nNOS) (Schmidt et al. (1991) *Biochem Biophys Res Comm* 181:1372–77), an inducible form (iNOS) is found in macrophages (Xie et al. (1992) *Science* 256:225–28; Lyons et al. (1992) *J Bio Chem* 267:6370–74), while another constitutive form is produced by endothelial cells (eNOS) (Janssens et al. (1992) *J Biol Chem* 267:14519–22). These are also known as Types I, II and III, respectively (Pollock et al. (1991) *Proc Natl Acad Sci USA* 88:10480–84).

The role of NO in the vascular system has been shown to be extensive (Vane et al. (1990) *New Eng J Med* 323:27–36). NO participates in the regulation of systemic blood pressure as evidenced by hypertension in mice in which the eNOS gene has been knocked out by homologous recombination (Huang et al. (1995) *Nature* 377:239–42). Decreasd responsiveness to NO in the pulmonary vasculature contributes to pulmonary hypertension while the vasodilator effects of NO are necessary for penile erection (Saenz et al. (1989) *New Eng J Med* 320:1025–30). Cutaneous vasculature has received some attention because the dermis has an extensive capillary network and these capillaries serve as a good model to study microcirculation in man. As in other blood vessels, the endothelium lining the dermal capillaries expresses eNOS. It has been observed that in the presence of NO, blood flow in the human skin microcirculation is remarkably increased and in the presence of inhibitors of NOS, vasodilatation is impaired (Warren, JB (1994) *FASEB J* 8:247–51; Ralevic et al. (1992) *Br J Pharmacol* 106:650–655).

Large amounts of NO are produced when macrophages are cultured with interferon-gamma (IFN-γ), tumor necrosis factor-alpha (TNF-α) or low doses of lipopolysaccharide (LPS) (Stuehr et al. (1985) *Proc Natl Acad Sci USA* 82:7738–42). Production of NO by macrophages is toxic to bacteria and parasites (Liew et al. (1991) *Immunol Today* 12(3):A17–A21). For example, resistance of mice to *Leishmania major* infection correlates with the induction of NOS in macrophages (Liew et al. (1990) *J Immunol* 144:4794–97). In mice where the iNOS gene has been knocked out, leishmania infection is severe.

The fact that NO is a neuronal messenger was first appreciated when it was shown that cerebellar granule cells release NO after exposure to glutamate agonists (Garthwaite, J. (1991) *Trends Neurosci* 14:60–67). NOS containing neurons are found throughout the central and peripheral nervous systems (Bredt et al. (1992) *Neuron* 8:3–11). NO plays a key role in nervous system morphogenesis and synaptic plasticity.

SUMMARY OF THE INVENTION

In one aspect, the invention features, a method of treating a subject, e.g., a human, for an unwanted epidermal or dermal condition. The method includes administering to the subject, a treatment which modulates the level of nitric oxide (NO) in the skin. Conditions characterized by unwanted cells, e.g., melanocytes or keratinocytes, the proliferation of such cells, or a deficiency in apoptosis of such cells, or unwanted pigmentation, are treated by increasing the level of NO in the skin. Conditions characterized by the lack of or by an insufficient number of dermal or epidermal cells, e.g., melanocytes or keratinocytes, or a lack of pigmentation, are treated by reducing the level of NO in the skin.

In preferred embodiments the epidermal or dermal condition is: a melanocyte-related disorder; a disorder characterized by a lack of skin or hair pigmentation, e.g., graying or other loss of pigmentation of the hair; a disorder characterized by unwanted or excess skin or hair pigmentation; a disorder characterized by a deficiency in the number or activity of melanocytes; a disorder characterized by unwanted melanocyte cell death; a disorder characterized by unwanted melanocyte apoptosis.

In preferred embodiments the condition is: vitiligo; post-inflammatory hypopigmentation; post-inflammatory hyperpigmentation; or idiopathic guttate hypomelanosis (IGH).

In preferred embodiments the epidermal or dermal condition is: a keratinocyte-related disorder; a disorder characterized by deficiency in the number or activity of keratinocyte; a disorder characterized by unwanted keratinocyte cell death; a disorder characterized by unwanted keratinocyte apoptosis.

In preferred embodiments the condition is characterized by unwanted keratinocyte proliferation, caused, e.g., by a deficiency in keratinocyte apoptosis.

In preferred embodiments the condition is: an inflammatory skin disorder, e.g., eczema or psoriasis; or toxic epidermal necrolysis (TEN).

In preferred embodiments the condition is lichen planus.

In preferred embodiments the condition is sunburn.

In preferred embodiments the condition is graft versus host disease (GvHD).

In other preferred embodiments: the treatment can be administered topically or intravenously. Preferably, the treatment is repeated, e.g., it is repeated at least 1, 2, 3, 4, or 5 times.

In preferred embodiments the treatment includes: the administration of a compound; the administration of a compound which inhibits the level of NO in the skin of the subject, e.g., an inhibitor of NO synthase or an NO scavenger, e.g., a heme compound, e.g., hemoglobin, thereby preferably decreasing the level of cell death (or increasing the number of viable) skin cells, e.g., melanocytes or keratinocytes.

In other preferred embodiments the treatment includes: the administration of a compound, e.g., the administration of a compound which increases the level of NO in the skin of the subject, e.g., an NO donor compound, e.g., sodium nitroprusside (SNP) or a derivative thereof, thereby preferably increasing the level of cell death (or decreasing the number of viable) skin cells, e.g., melanocytes or keratinocytes.

In preferred embodiments the level of NO in the skin is modulated by inhibiting the production of NO by a Langerhans cell or a keratinocyte.

In other preferred embodiments the modulation results in: a decrease in the level of melanocytes or keratinocytes; a decrease in the level of cell death of melanocytes or keratinocytes.

In another aspect, the invention features, a method of treating a subject for a loss of pigmentation in the hair. The method includes administering to the subject a treatment which decreases the level of nitric oxide (NO) in the skin, e.g., in the scalp.

The treatment can be administered topically or subcutaneously, e.g., to the scalp, or intravenously and can be repeated, e.g., repeated at least 1, 2, 3, 4, or 5 times.

In preferred embodiments the treatment includes: the administration of a compound; the administration of a compound which inhibits the level of NO in the skin of the subject, e.g., an inhibitor of NO synthase or an NO scavenger, e.g., a heme compound, e.g., hemoglobin, thereby preferably decreasing the level of melanocyte cell death.

In preferred embodiments the level of NO in the skin is modulated by: inhibiting the production of NO by a Langerhans cell or a keratinocyte.

In another aspect, the invention features, a method of treating a subject, e.g., a human, for sunburn or other exposure to ultra-violet light, or for unwanted effects of aging on the skin. The method includes administering to the subject a treatment which decreases the level of nitric oxide (NO) in the skin.

The treatment can be administered topically or subcutaneously, e.g., to the affected area of the skin, or intravenously and can be repeated, e.g., repeated at least 1, 2, 3, 4, or 5 times.

In preferred embodiments the treatment includes: the administration of a compound; the administration of a compound which inhibits the level of NO in the skin of the subject, e.g., an inhibitor of NO synthase or an NO scavenger, e.g., a heme compound, e.g., hemoglobin, thereby preferably decreasing the level of melanocyte or keratinocyte cell death.

In preferred embodiments the level of NO in the skin is modulated by: inhibiting the production of NO by a Langerhans cell or a keratinocyte.

In another aspect, the invention features, a method of treating a subject, e.g., human, for toxic epidermal necrolysis. The method includes administering to the subject a treatment which decreases the level of nitric oxide (NO) in the skin.

The treatment can be administered topically or subcutaneously, e.g., to the affected area of the skin, or intravenously and can be repeated, e.g., repeated at least 1, 2, 3, 4, or 5 times.

In preferred embodiments the treatment includes: the administration of a compound; the administration of a compound which inhibits the level of NO in the skin of the subject, e.g., an inhibitor of NO synthase or an NO scavenger, e.g., a heme compound, e.g., hemoglobin, thereby preferably decreasing the level of melanocyte or keratinocyte cell death.

In preferred embodiments the level of NO in the skin is modulated by: inhibiting the production of NO by a Langerhans cell or a keratinocyte.

In another aspect, the invention features, a method of treating a subject for vitiligo. The method includes administering to the subject a treatment which decreases the level of nitric oxide (NO) in the skin.

The treatment can be administered topically or subcutaneously, e.g., to the affected area of the skin, or intravenously and can be repeated, e.g., repeated at least 1, 2, 3, 4, or 5 times.

In preferred embodiments the treatment includes: the administration of a compound; the administration of a compound which inhibits the level of NO in the skin of the subject, e.g., an inhibitor of NO synthase or an NO scavenger, e.g., a heme compound, e.g., hemoglobin, thereby preferably decreasing the level of melanocyte or keratinocyte cell death.

In preferred embodiments the level of NO in the skin is modulated by: inhibiting the production of NO by a Langerhans cell or a keratinocyte.

In another aspect, the invention features, a method of altering the appearance of the skin, preferably decreasing pigmentation, or generally, lightening the skin, in a subject, e.g., a human. The method includes administering to the subject, a treatment which increases the level of nitric oxide (NO) in the skin.

In preferred embodiments: the treatment can be administered topically or intravenously. Preferably, the treatment is repeated, e.g., it is repeated at least 1, 2, 3, 4, or 5 times.

In other preferred embodiments the treatment includes: the administration of a compound, e.g., the administration of a compound which increases the level of NO in the skin of the subject, e.g., an NO donor compound, e.g., sodium nitroprusside (SNP) or a derivative thereof, thereby preferably increasing the level of cell death (or decreasing the number of viable) skin cells, e.g., melanocytes or keratinocytes.

In another aspect, the invention features, a method of altering the appearance of the skin, preferably increasing pigmentation, or generally, darkening the skin, in a subject, e.g., a human. The method includes administering to the subject, a treatment which decreases the level of nitric oxide (NO) in the skin.

In preferred embodiments: the treatment can be administered topically or intravenously. Preferably, the treatment is repeated, e.g., it is repeated at least 1, 2, 3, 4, or 5 times.

In preferred embodiments the treatment includes: the administration of a compound; the administration of a compound which inhibits the level of NO in the skin of the subject, e.g., an inhibitor of NO synthase or an NO scavenger, e.g., a heme compound, e.g., hemoglobin, thereby preferably decreasing the level of cell death (or increasing the number of viable) skin cells, e.g., melanocytes or keratinocytes.

In another aspect, the invention features, a method of altering the appearance of the hair, preferably decreasing pigmentation, or generally, lightening the hair, in a subject, e.g., a human. The method includes administering to the subject, a treatment which increases the level of nitric oxide (NO) in the skin, e.g., the scalp.

In preferred embodiments: the treatment can be administered topically or intravenously. Preferably, the treatment is repeated, e.g., it is repeated at least 1, 2, 3, 4, or 5 times.

In other preferred embodiments the treatment includes: the administration of a compound, e.g., the administration of a compound which increases the level of NO in the skin of the subject, e.g., an NO donor compound, e.g., sodium nitroprusside (SNP) or a derivative thereof, thereby preferably increasing the level of cell death (or decreasing the number of viable) skin cells, e.g., melanocytes or keratinocytes.

In another aspect, the invention features, a method of altering the appearance of the hair, preferably increasing pigmentation, or generally, darkening the hair, in a subject, e.g., a human. The method includes administering to the subject, a treatment which decreases the level of nitric oxide (NO) in the skin, e.g., the scalp.

In preferred embodiments: the treatment can be administered topically or intravenously. Preferably, the treatment is repeated, e.g., it is repeated at least 1, 2, 3, 4, or 5 times.

In preferred embodiments the treatment includes: the administration of a compound; the administration of a compound which inhibits the level of NO in the skin of the subject, e.g., an inhibitor of NO synthase or an NO scavenger, e.g., a heme compound, e.g., hemoglobin, thereby preferably decreasing the level of cell death (or increasing the number of viable) skin cells, e.g., melanocytes or keratinocytes.

The inventors have discovered that transgenic animals having one or more constructs which include a skin promoter coupled to a gene which increases the level of NO in the skin, can be used to evaluate a compound for use in enhancing the health or appearance of the hair or skin, particularly pigmentation of the hair or skin.

Accordingly, the invention features, a method of evaluating a compound for its effect on the hair or skin. The method includes:

providing a transgenic animal having a gene which increases the level of NO in the skin coupled to a skin promoter;

administering the compound to the transgenic animal; and evaluating the compound for its effect on the hair or skin.

In preferred embodiments, the compound is administered by: applying the compound to the hair or skin of the transgenic animal; systemically administering the compound; orally administering the compound; or injecting the compound, preferably dermally or subcutaneously. In preferred embodiments, the compound is administered using a suitable delivery vehicle, for example, a surfactant or an agent which increases permeability in the skin, e.g., an SDS or DMSO containing formulation.

In preferred embodiments, the transgenic animal is a non-human transgenic animal. For example, the transgenic animal can be a transgenic mini-pig, a transgenic guinea-pig, a transgenic rat, or a transgenic mouse. The most preferred animals are mice.

In particularly preferred embodiments, the skin promoter is: an involution promoter; a keratin, e.g., a keratin 14, promoter; a tyrosinase promoter.

In preferred embodiments gene encodes: a nitric oxide synthase, e.g., inducible nitric oxide synthase.

In preferred embodiments, the method further includes one or more subsequent administrations of the compound to the transgenic animal. In preferred embodiments, the compound is administered to the transgenic animal for a period of at least one, two, three, or four weeks. The compound can be administered at a constant level or at a range of different levels.

In preferred embodiments, the compound is: a cosmetic; a non-toxic substance; a substance approved for human drug or cosmetic use in one or more jurisdictions.

In another aspect, the invention features, a non-human transgenic animal described herein, e.g., a transgenic animal having gene which increases the level of NO in the skin, e.g. the iNOS gene, coupled to a skin promoter. e.g. an involucrin promoter; a keratin, e.g., a keratin 14, promoter; a tyrosinase promoter.

In preferred embodiments, the transgenic animal is a non-human transgenic animal. For example, the transgenic animal can be a transgenic mini-pig, a transgenic guinea-pig, a transgenic rat, or a transgenic mouse, e.g., a senescence accelerated mouse, or a transgenic mutant mouse which exhibits a phenotype of accelerated aging. The most preferred animals are mice.

In another aspect, the invention features a promoter- gene construct described herein.

Methods of the invention can be performed in vivo, with whole animals, or in vitro, that is, with tissue, e.g., skin, or cells, which are derived from a transgenic animal described herein or with cells, preferably skin cells or tissue, from cells transformed with a promoter/gene construct.

The methods of the invention allow rapid and efficient evaluation of compounds for their effect on skin or hair.

As used herein, the term "epidermal or dermal condition" refers to any unwanted condition, e.g., a disorder, a disease, an autoimmune disorder, or a condition of the hair or skin associated with aging, stress, or exposure to sun.

As used herein, the term "modulates" refers to increasing or decreasing levels of NO in the skin (or hair) of a subject. For example, NO levels in the skin can be decreased by administration, e.g., topical or intravenous administration, of an inhibitor of NO synthase or an NO scavenger, e.g., a heme compound, e.g., hemoglobin. The levels of NO in the skin can be increased by administration, e.g., topical or intravenous, of an NO donor, e.g., sodium nitroprusside (SNP) or a derivative thereof. Modulation can occur at the level of the gene, e.g., by gene or cell therapy, e.g., to increase NO synthesis, at the level of gene expression, e.g., by administration of antisense molecules which inhibit NOS expression, at the enzyme level, e.g., by the addition of an inhibitor of NOS, or at the product level, e.g., by the addition of a scavenger molecule or by absorbing NO, or by administration of NO.

The term "subject," as used herein, is intended to include mammals having or being susceptible to an unwanted epidermal or dermal condition. Examples of such subjects include humans, dogs, cats, pigs, cows, horses, rats and mice.

The term "treating a condition" is intended to include preventing, inhibiting, reducing, or delaying the progression of the condition.

As used herein, a "transgenic animal" is an animal, e.g., a non-human mammal, e.g., a mini-pig, a guinea-pig, or a rodent, e.g., a mouse or a rat, in which one or more, and preferably essentially all, of the cells of the animal include a transgene. The transgene can be introduced into the cell, directly or indirectly by introduction into a precursor of the cell, e.g., by microinjection, transfection or infection, e.g., by infection with a recombinant virus. The term genetic manipulation is directed to the introduction of a recombinant DNA molecule. This molecule may be integrated within a chromosome, or it may be extrachromosomally replicating DNA.

As used herein, the term "rodent" refers to all members of the phylogenetic order Rodentia.

As used herein, the term "skin promoter" refers to a promoter which is transcriptionally active in the skin. It need not be skin-specific. The gene in which the promoter is naturally found can be a gene involved in the maintenance, or proper functioning of the skin.

As used herein, "administering a compound to an animal" refers to dispensing, delivering or applying a treatment to an animal or cell. Administration can be by topical administration, by parenteral or oral route, intramuscular injection, subcutaneous/intradermal injection, intravenous injection, buccal administration, transdermal delivery or administration by the intranasal or respiratory tract route. The most preferred administrations are topical application or subcutaneous or intradermal injection.

The inventors have discovered that NO is an important mediator in skin physiology. Methods of the invention can treat pathological processes in the skin, resolve diagnostic dilemmas and enhance therapeutic measures available to dermatologists.

There are many patients whose skin disease is exacerbated by stress. One possible explanation for this phenomenon is that nerves release mediators that stimulate Langerhans cells to produce iNOS resulting in the production of large amounts of NO with associated alteration of normal physiological processes or immune function. Thus, blockade of NOS will have beneficial effects.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

Other features and advantages of the invention will be apparent from the following detailed description, and from the claims.

BRIEF DESCRIPTION OF THE INVENTION

The drawings will first be briefly described.
Drawings

Figure 1B:
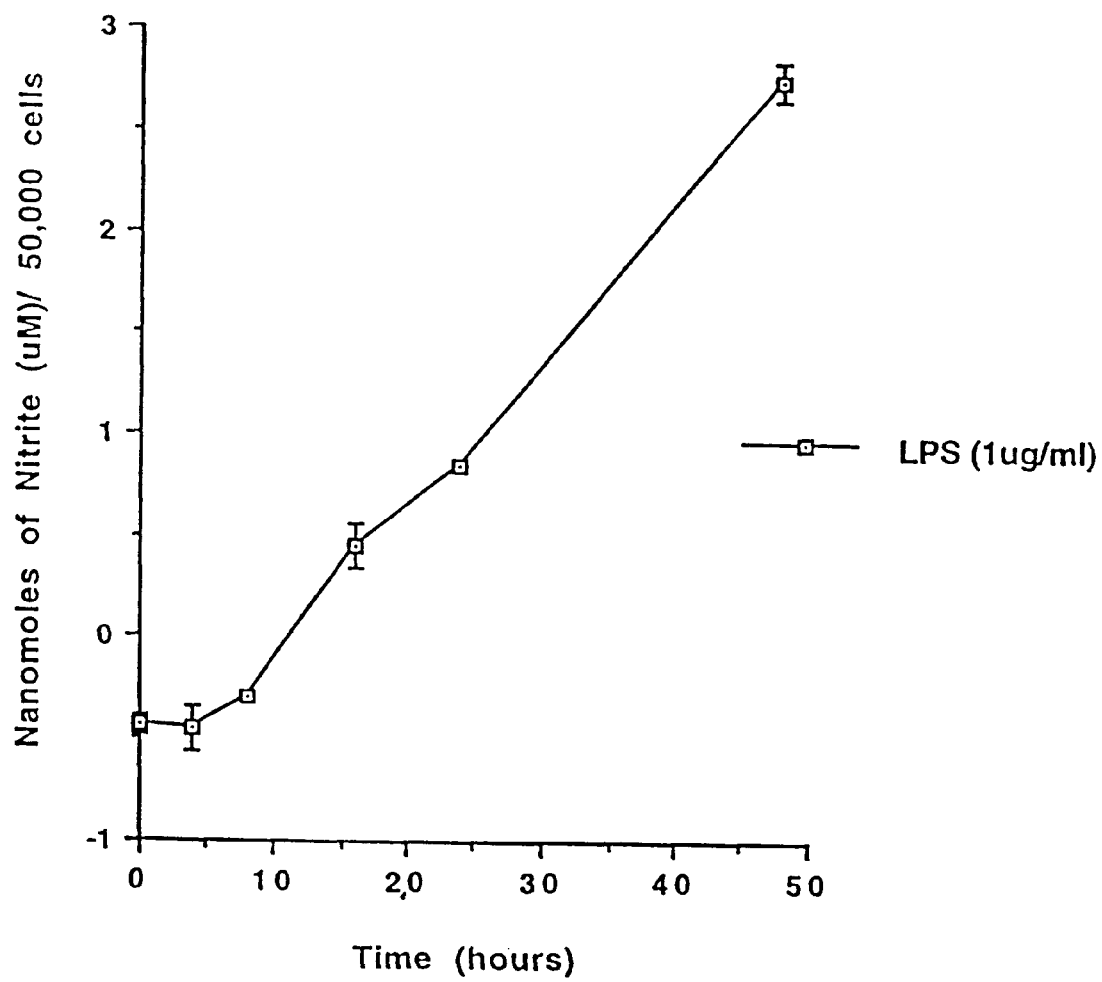

FIGS. 1A and 1B: A graph depicting LC and SX-52 cells NO production in the presence of LPS. A. Nitrite levels of supernatants from SX-52 cells after 24 hours (200,000 cells/well). B. NO production increases over time in XS-52 cells (50,000 cells/well). Experiments were performed in triplicate, and bars represent the average with standard deviation.

Figure 2:
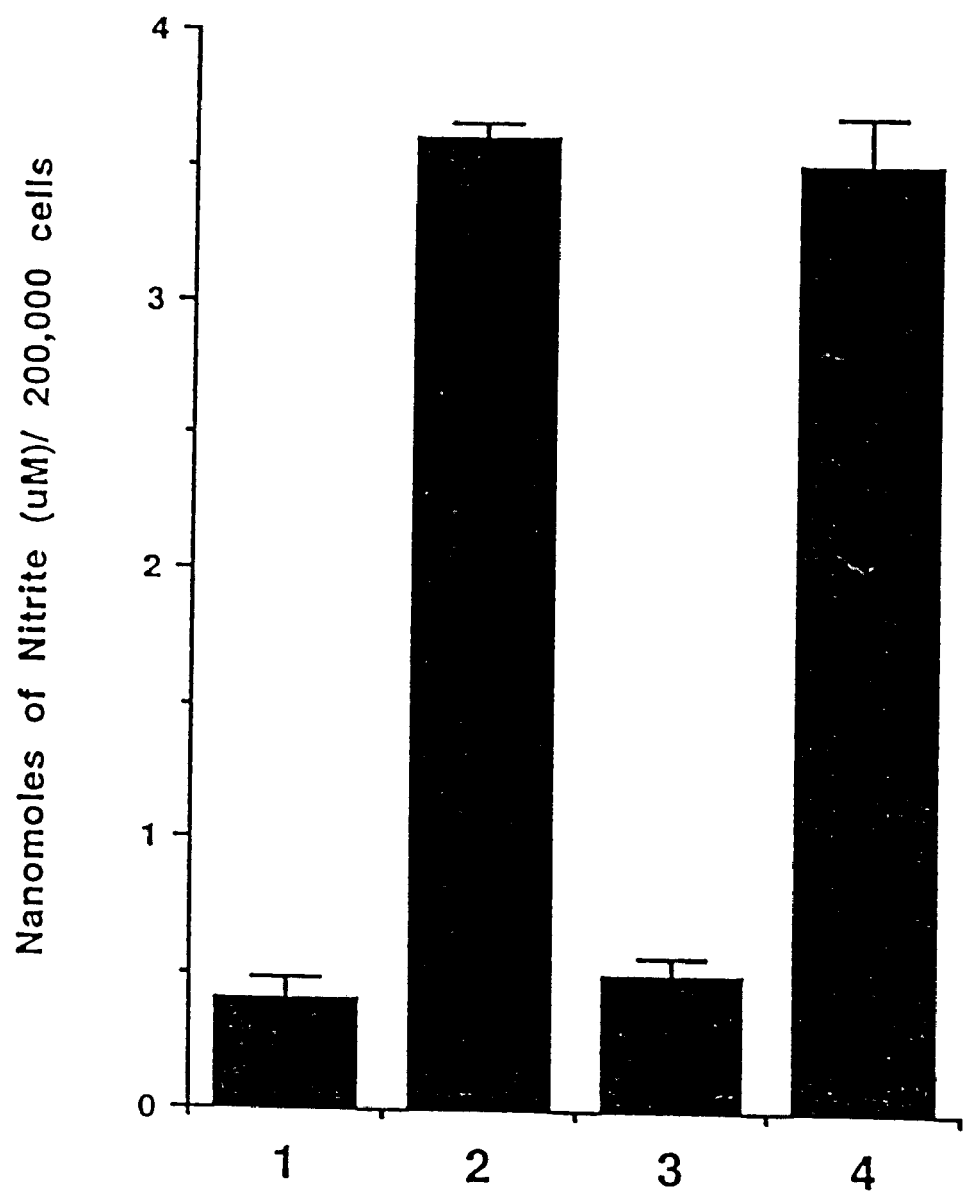

FIG. 2: A bar graph depicting inhibition of NO production in XS-52 cells by L-NAME. Supernatants from SX-52 cells incubated overnight at 37° C. in LPS (1 µg/ml) with L-NAME- an inhibitor of iNOS, were assayed for nitrite levels using the Griess reaction (200,000 cells/well). The bars represent an average of three wells on a microtiter plate. 1=(LPS(−), 2-LPS(+) 1 µg/ml, 3+LPS+L-NAME (5 mM), 4=LPS+D-NAME (5 mM).

Figure 3:
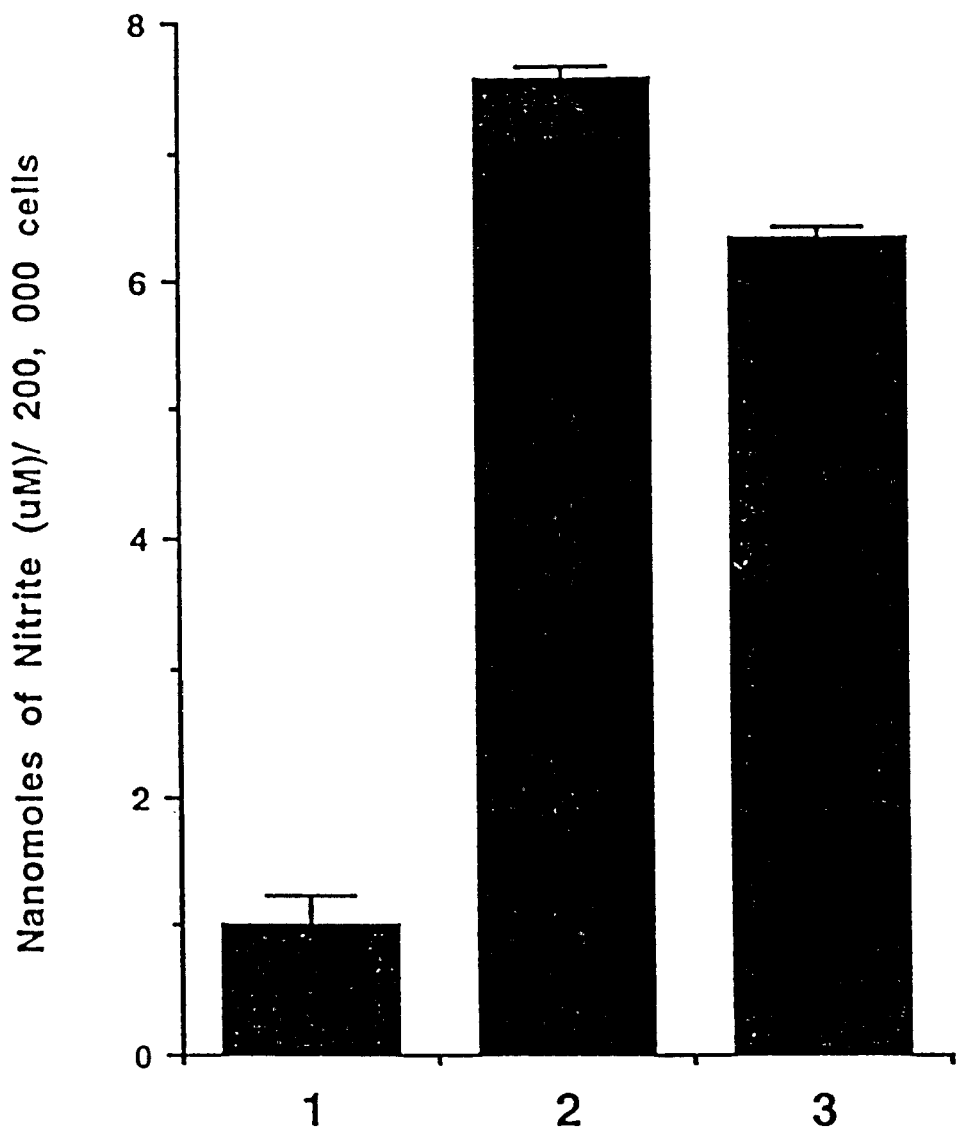

FIG. 3: A bar graph depicting IL-10 suppression of NO production in XS-52 cells. IL-10 suppresses NO production as seen by bar 3, compared to optimal NO production in the presence of LPS alone (bar 2). IL-10 (10 ng/ml) actually effects iNOS induction, but the effect can also be seen at the level of the final product, NO. All bars are shown with standard deviation.

Figure 4:
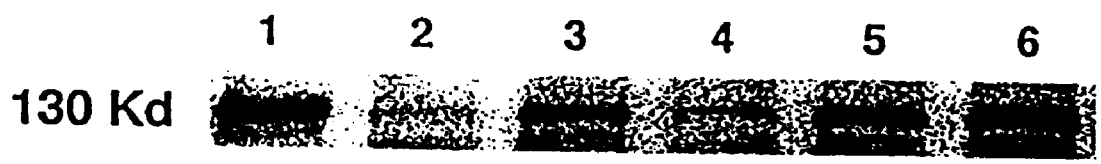

FIG. 4: A photograph of a gel depicting IL-10 inhibition of iNOS expression. Western blot with a control (1) RAW 264.7 (mouse macrophage cell-line) cell extract demonstrates increase in iNOS expression in the presence of LPS (3), which is inhibited by IL-10. L-NAME and D-NAME do not affect iNOS levels in XS-52 cells. 1=RAW 264.7 cells (LPS), 2=LPS(−), 3=LPS(+), 4=LPS+IL-10 (50 ng/ml), 5=LPS+L-NAME (5 mM), 6=LPS+D-NAME (5 mM).

LANGERHANS CELLS AND NO

Langerhans cells (LC) are dendritic cells of the skin that play a key role in cutaneous immune responses. They can be considered as sentinels standing guard against external stimuli. Their function is to sample, respond themselves and to inform the rest of the immune system of changes in the environment. LC reside in the basal and suprabasal layers of the epidermis and form a network of dendrites, through which they interact with adjacent keratinocytes and nerves. They are mobile, and can migrate to the T cell dependent area of lymph nodes. Like macrophages they are bone-marrow derived, constitutively express MHC-II and have potent antigen presenting properties. Unlike macrophages however, LC have the ability to sensitize naive T cells.

In 1981, Tannenbaum found that a patient who suffered from infectious diarrhea excreted very high levels of urinary nitrates, opening the door to a series of investigations which resulted in the discovery of nitric oxide (NO) in macrophages (Snyder et al. (1992) *Sci Amer* 5:68–77). It is now known that macrophages express an inducible isoform of the enzyme nitric oxide synthase (iNOS) whose gene has been cloned and the expression of which is dramatically increased in the presence of the endotoxin, lipopolysaccharide (LPS) (Xie et al. (1992) *Science* 256:225–28; Lyons et al. (1992) *J Bio Chem* 267:6370–74). iNOS is responsible for converting L-arginine into NO via a series of redox reactions involving cofactors such as tetrahydrobiopterin. Nitric oxide is a short-lived, highly reactive gas that has the ability to diffuse across cells and can cause effects in neighboring cells. Thus it may be produced distant to its actual site of action. Potentially toxic, NO has rich redox and additive chemical properties which allow it to exert paradoxical effects in related biological systems. It is both a messenger and an effector (toxin). It is a mediator in vasodilatation, a neurotransmitter in the central and peripheral nervous systems and an active agent in macrophage cytotoxicity and neurotoxicity. NO has also been identified as a neurotransmitter and an isoform of the enzyme iNOS is expressed in nerves (neuronal NOS, ncNOS). NO from macrophages has been implicated in the non-specific defense against parasitic disease as it participates in the production of free radicals which are directly toxic to bacteria and parasites. Thus, NO mediates both servoregulatory and cytotoxic functions and this may be due to its biochemical properties which allow it to exert paradoxical effects in related systems.

Though NO has not been described with great detail in the skin, it has been demonstrated to play a role in cutaneous vasodilatory responses, Substance P induced edema formation in mouse skin and mustard-oil induced inflammation in rat skin. The skin is the first defense against a hostile environment. Therefore, it must have an efficient immune system to tackle a variety of potentially harmful organisms and substances. Langerhans cells form the afferent arm of this system. In the epidermis, although macrophages can be recruited, the Langerhans cell is the major antigen presenting cell. Nitric oxide is an important effector molecule in macrophages.

Although not wishing to be bound by theory, the Applicants believe that keratinocytes may also be responsible for the production of NO by nitric oxide synthase.

Inhibitors of NO Synthesis

As used herein, the term "NO synthase inhibitor" refers to any competitive or non-competitive inhibitor of NO synthase. The effectiveness of a compound, and its relative potency as an NOS inhibitor, can be tested and routinely determined by measuring inhibition of NOS activity by monitoring the conversion of arginine to citrulline by NOS in, for example, cerebellar homogenates. A reduction in citrulline formation indicates inhibitory activity of the compound. The percent reduction in citrulline formation, compared to the amount of citrulline formed in the absence of the compound being tested, indicated the potency of the compound as an NOS inhibitor.

Inhibitors of nitric oxide synthase which can be used in this invention include substrate analogs, such as aminogunidin, $N^G$-nitro-L-arginine, $N^G$-methyl-L-arginine, $N^G$-nitro-L-arginine, $N^G$-nitro-L-argine methyl ester, and $N^G$-iminoethyl-L-ornithine, flavoprotein binders, such as diphenylene iodonium, iodomium dipheny and di-2-thienyl iodonium, calmodulin binders, such as calcineurin, trifluoroperazine, N-(4-aminobutyl)5-chloro-2-naphthalenesulfonamide and N-(6-aminohexyl)-1-naphthalenesulfonamide, heme binders, such as carbon monoxide, depleters and analogs of tetrahydrobiopterin, such as 2,4-diamino-6-hydroxypyrimidine, and induction inhibitors, such as corticosteroids, TGF-$\beta^c$-1, -2, 3, interleukin-4, interleukin-10 and macrophage deactivation factor (Nathan, the FASEB Journal, Vol. 6, September 1992, pp. 3051–3064). Preferred are the substrate analogs of nitric oxide synthase, $N^G$-amino-L-arginine, $N^G$-methyl-L-arginine, $N^G$-nitro-L-arginine $N^G$-nitro-L-arginine methyl ester, and $N^G$-iminoethyl-L-ornithine. Particularly preferred are $N^G$-amino-L-arginine, $N^G$-methyl-Larginine, $N^G$-nitro-L-arginine, and aminoguanidine. Most preferred is $N^G$-methyl-L-arginine. Many of these inhibitors are available from commercial sources, e.g., Calbiochem, Sigma, and Aldrich.

Pharmaceutically acceptable salts may also be administered. Examples of suitable salts include acid salts, such as hydrogen chloride, hydrogen bromide, hydrogen iodide, sulfate and acetate salts, as well as basic salts, such as amine, ammonium, alkali metal and alkaline earth metal salts.

In another embodiment, an inhibitor of the NO synthase cofactor tetrahydropterin can be used. One such inhibitor is aminopterin.

Nitric Oxide (NO) Scavengers

As used herein, the term "NO scavenger" refers to a molecular entity that binds with free NO so as to reduce the concentration of NO locally or systemically. Such scavengers include, but are not limited to, metalloproteins, in particular heme containing proteins such as but not limited to hemoglobin, myoglobin, cytochrome-P-450, heme albumin, heme-containing peptides such as undecapeptide of cytochrome C, as well as water soluble hemoglobin analogs such as strapped heme (e.g., Traylor and Traylor (1982) Ann. Rev. Biophys. Bioeng 11:105–127) and picket fence porphyrin (Collman et al. (1975) J Am. Chem. Soc. 97:1427–1439). In a preferred embodiment, the scavenger selected for use is one which, in vivo, in vitro, or animal model experiments, is shown to be capable of causing vascular stasis that is not reversed by L-arginine.

Use of many scavengers according to the present invention has the advantage of restriction NO reduction to the vasculature, without affecting intracellular NO production or extravascular NO activity. Thus, NO activity as a transduction mechanism for soluble guanylate cyclase in the nervous system and the function of immune cells, such as macrophages, will be minimally affected, thus reducing possible side effects of therapy with an NO scavenger.

Other Inhibitors of NO Activity

In addition to inhibitors of NO synthase, methods of the invention can use inhibitors of the second messenger system activated by NO, particularly the second messengers (downstream signal mediators) guanylate cyclase and cyclic CMP. A non-limiting example of guanylate cyclase inhibition is methylene blue. Cyclic GMP activity can be inhibited by aminoguanidine, such as M&B 22948.

Reversal of NO Synthesis Inhibition in Normal Tissue

Methods of the invention can include the therapeutic administration of an NO synthase inhibitor (a competitive inhibitor, e.g., a substrate analog) followed by administration of an NO synthase substrate so as to selectively reverse any effect of the inhibitor on normal tissue.

NO synthase substrates which can be used, but are not limited to, are guanidine succinate and L-arginine.

NO Donors

Methods of the invention can include the therapeutic administration of an NO donor. As used herein, the term "NO donor" refers to a molecular entity which is capable of releasing NO. Examples of NO donors include sodium nitroprusside (SNP) or derivatives thereof.

Transgenic Animals

Transgenic animals which can be used in the methods of the invention include non-human mammals, such as pigs, e.g., mini-pigs, or guinea-pigs; or rodents, e.g., mice or rats. The transgenic animals can be homozygous or heterozygous for the transgene. Mice are a preferred subject animal.

Methods for the preparation of a variety of animals are known in the art. A protocol for the production of a transgenic pig can be found in White and Yannoutsos, Current Topics in Complement Research: 64th Forum in Immunology, pp. 88–94; U.S. Pat. No. 5,523,226; U.S. Pat. No. 5,573,933; PCT Application WO93/25071; and PCT Application WO95/04744. A protocol for the production of a transgenic rat can be found in Bader and Ganten, Clinical and Experimental Pharmacology and Physiology, Supp. 3:S81–S87, 1996. A protocol for the production of a transgenic cow can be found in Transgenic Animal Technology, A Handbook, 1994, ed., Carl A. Pinkert, Academic Press, Inc. A protocol for the production of a transgenic sheep can be found in Transgenic Animal Technology, A Handbook, 1994, ed., Carl A. Pinkert, Academic Press, Inc. All patents and references are incorporated herein by reference.

Pharmaceutical Compositions

The compounds of the claimed invention can be administered alone or in a suitable pharmaceutical composition. Modes of administration are those known in the art, such as enteral, parenteral, e.g., intravenous, or topical application. Intravenous administration is preferred and topical administration is particularly preferred.

Preferably the compound is prepared in an admixture with a pharmaceutically acceptable carrier. The term "carrier"

refers to diluents, excipients and the like for use in preparing admixtures of a pharmaceutical composition. Suitable pharmaceutical carriers can be employed and include, but are not limited to water, salt solutions, alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, flavorants, coloring, and/or aromatic substances and the like which do not deleteriously react with the active compounds.

For parenteral application, particularly suitable are injectable, sterile solutions, preferably oily or aqueous solutions, as well as suspensions, emulsions, or implants, including suppositories. Ampoules are convenient unit dosages. Oral applications are preferably administered in the forms of capsules, tablets and/or liquid formulations. Unit form dosages are preferred.

The dosage and length of treatment depends on the disease state being treated. The duration of treatment may be a day, a week or longer and may, as it the case of a chronic progressive condition last over the entire lifetime of the patient. The compounds of the invention may also be administered on a daily basis as long as the symptoms persist. The inhibitors are administered in a therapeutically effective amount, a typical human dosage of NO synthase inhibitor ranging from about 0.01 mg/kg of body weight to about 10 mg/kg, in single or divided doses. The dosage will vary depending on the NO synthase inhibitor or scavenger to be used and its relative potency. Dosage and length of treatment are readily determinable by the skilled practitioner based on the condition and stage of disease.

Generally, the compound is administered in a single bolus dose, although the present invention also contemplates sustained administration, e.g., via an IV drip or pump, or administration in multiple boluses.

The compounds of the invention are preferably incorporated in a topical composition or a cosmetic composition which includes a non-toxic dermatologically acceptable vehicle or carrier which is adapted to be spread upon the skin. Examples of suitable vehicles are acetone, alcohols, or a cream, lotion, or gel which can effectively deliver the active compound. One such vehicle is disclosed in PCT/US93/05068. In addition, a penetration enhancer may be added to the vehicle to further enhance the effectiveness of the formulation.

The concentration of the compound of the invention in the topical composition may be varied over a wide range up to a saturated solution, preferably from 0.01% to 30% by weight or even more. The maximum amount effectively applied is limited only by the rate at which the compound of the invention penetrates the skin. Generally, the effective amounts range from 10 to 3000 micrograms or more per square centimeter of skin.

Techniques and formulations for administering the compositions may be found in *Remington's Pharmac eutical Sciences,* Meade Publishing Col., Easton, Pa., latest edition.

Assaying Nitric Oxide (NO) Levels

The short half life (six seconds), instability in the presence of oxygen and small amounts produced make direct measurement of NO difficult but possible with NO-sensitive electrodes (Archer S. (1993) *FASEB J* 7:349–60). Functional assays focus on the presence of nitric oxide synthase (NOS), the enzyme which catalyzes the formation of NO via oxidation of the guanidino-nitrogen in L-arginine producing NO and citrulline. Indirect assays employ the Griess Reaction to measure nitrite, one of the oxidation products of NO (Green et al. (1982) *Analytical Biochem* 126:131–38). Determination of levels of the second messenger cyclic GMP (cGMP) assess the effect of NO on the enzyme guanylate cyclase that is activated by NO to produce cGMP (McKee et al. (1994) *Proc Natl Acad Sci USA* 91:12056–60). Detection of NOS RNA on Northern blots and NOS protein on Western blots provides additional avenues to study NO regulation. Histochemistry can be employed to examine the expression of NOS in situ. All of these tools can be employed to study the contribution of NO to cutaneous physiology.

This invention is further illustrated by the following examples which in no way should be construed as being further limiting. The contents of all cited references (including literature references, issued patents, published patent applications, and copending patent applications) cited throughout this application are hereby expressly incorporated by reference.

EXAMPLES

The Following Materials and Methods were Used in Examples 1–6

Animals

Eight to twelve week old BALB/c mice were obtained from The Jackson Laboratory (Bar Harbor, Me.) for preparation of LC.

Tissue Culture Reagents, Media and Chemicals

Tissue culture reagents were obtained from Life Technologies, Grand Island, N.Y.; complete media (CM), consisted of RPMI 1640 supplemented with 10% fetal calf serum (FCS), hepes (10 mM), streptomycin (100 $\mu$g/ml), penicillin (100 U/ml), 2-mercapto-ethanol (0.1 M), sodium pyruvate (1 mM), non-essential amino acids (0.1 mM) and L-glutamine (2 mM). Recombinant murine IL-10 was obtained from Biosource and LNAME and D-NAME from Sigma, St. Louis, Mo.

Antibodies and related reagents were as follows: anti-Thy-1.2 mAb, (Sigma), low-toxicity rabbit complement (Cedarlane, Homby, Ontario, Canada), mouse anti-mouse I-A$^d$ (Pharmingen, San Diego, Calif.), goat anti-mouse IgG conjugated to magnetic microspheres (Dynabeads M-450; Dynal A. S, Oslo, Norway), Lympholyte M (density 1.0875, Cedarlane, Homby, ON) and anti-iNOS FITC conjugated monoclonal antibody (IgG) to a 21 kDa protein fragment corresponding to amino acids 961–1144 of mouse macrophage NOS (Transduction laboratories, Lexington, Ky.). All other chemicals were obtained from Sigma.

EC Preparation

Monocellular suspensions of murine EC were prepared as reported previously. Thy-1+cells were depleted by incubation with anti-Thy-1.2 mAb and complement. Dead cells were removed over Lympholyte M. Interface cells were washed and subjected to magnetic microsphere separation to isolate LC using mouse anti-mouse I-A$^d$ for 30 minutes followed by incubation with goat anti-mouse IgG conjugated to magnetic microspheres and subjected to a magnetic field. Cells with magnetic spheres on their surface were separated based on the magnetic field. Those with attached magnetic beads were designated LC. LC were cultured in serum-free CM.

Langerhans Cell-like Cell Line (XS-52)

A dendritic cell line was established from newborn BALB/c epidermis as previously described. This cell line has features of Langerhans cells, i.e., cells are dendritic, contain Birbeck granules, present antigen and have many phenotypic characteristics of freshly harvested LC. The cell line was propagated in RPMI 1640 containing 10% FCS, 50 U/ml recombinant murine GM-CSF and 10% NS cell supernatant (supernatants from stromal cells cultured from newborn BALB/c mice). These cells were grown in CM without GM-CSF and NS cell supernatant for two days prior to experiments.

Reverse Transcriptase-PCR

PolyA$^+$ RNA was extracted from purified LC incubated with and without LPS using magnetic microspheres (Dynabeads mRNA DIRECT kit, Dynal, Oslo, Norway) and RT-PCR was performed (Geneamp RNA PCR kit, Perkin Elmer, Branchburg, N.J.). Degenerate primers (sequences received with thanks from Dr. Johanna Wolframm, Dept. of Cardiology, University of Vienna, Austria) designed to amplify iNOS, ecNOS or ncNOS, and across mouse, rat and human species; 5' primer (Deg-A), CAYRTCAAGTAYGC-CACCAACAAAGGGAA and 3' primer (Deg-C), RCCRATCTCHGTGCYCATGTACCWRC. These primers span 419 base pairs in the mouse macrophage-iNOS sequence. PCR conditions were as follows: RT reaction-room temperature for 20 mins, 42° C. for 15 mins, 99° C. for 5 mins, and 5° C. for 5 min; PCR reaction –94° C. for 3 mins, denaturing –94° C. 30 sec, annealing –55° C. 30 sec, extension –72° C. 1 min–40 cycles, 72° C. for 7 mins, 4° C. PCR products were separated in 1.5% agarose gels and stained with ethidium bromide. The fragment obtained was gel purified, cloned (TA cloning kit, Invitrogen, Sorrento Valley, Calif.), and sequenced (Sequenase 2.0, USB, Ocala, Fla.).

PolyA$^+$ RNA from XS-52 cells (extracted as above) was subjected to PCR with iNOS-specific primers; 5' primer (iNOS-A), AGCATCAGAGGGGATGCTGC and 3' primer (iNOS-C), ATCCTTCGGCCCACTTCCTC. These primers span 370 bp in the mouse macrophage-iNOS sequence; iNOS-A (992–1011 nucleotides), and iNOS-C (1362–1343 nucleotides). These reactions were carried out in parallel with GAPDH primers to standardize intensity of bands obtained with and without LPS. After RT reaction, the reaction mixture was split for PCR for iNOS (40 cycles) and GAPDH (25 cycles). Primers for GAPDH were chosen from homologous region between human, chick and rat species; 5' primer (GAPDH-A), ACTACATGGTTTACATGTTC and 3' primer (GAPDH-C), TTCCCGTTCAGCACTGGGATGA for nucleotides 183–201 and 740–719 respectively for human GAPDH cDNA. As a control, mouse ncNOS-specific primers were also used.

Immunoflourescence Staining

XS-52 cells were grown for two days in eight-well chamber slides (Nunc Inc., Naperville, Ill.), washed with cold PBS, fixed with 1:1, methanol:acetone for 5 minutes, permeabilized with 0.2% Triton-X 100 in PBS for 20 minutes and blocked with 2% horse serum. After two washes in 0.2% BSA in PBS, anti-iNOS FITC was added to the wells at a 1:100 dilution and incubated at 37° C. for 1 hour. After three washes with PBS, each 10 minutes, the slides were mounted with Gel/mount (Biomeda, Foster City, Calif.).

Griess Reaction (Nitrite Measurement)

XS-52 cells were incubated in 24 well plates, in both, the presence and absence of LPS (1 μg/ml). After 24 hrs at 37° C., the supernatants from respective wells were assayed for the presence of nitrite using the Saville modification of the Griess reaction(Green et. al. (1982) *Analytical Biochem* 126:131–38). 50 μl aliquots of cell-free supernatants from cells cultured with and without LPS, L-NAME or IL-10 were incubated with 50 μl of 1% sulfanilamide in 0.5N HCl, and 50 μl of 0.02% naphthylethyiene diamine dihydrochloride for 5 minutes at room temperature in flat-bottom 96 well plates. Absorbance was measured at 540 nm in an ELISA plate-reader. Sodium nitrite was used as a standard for quantification of nitrite in culture supernatants.

Western blot with anti-iNOS antibody

XS-52 cells grown for two days in CM without GM-CSF in 24 well plates were treated with LPS (1 μg/ml), LPS+IL-10 (50 ng/ml), LPS+L-NAME (5 mM) and LPS+D-NAME (5 mM) for 24 hrs at 37° C. Cells were washed with serum-free media, and boiling SDS gel-loading buffer (2×: 100 mM Tris.Cl [pH 6.8], 200 mM Dithiothreitol, 4% SDS, 0.2% bromophenol blue, and 20% glycerol) was added. The cells were scraped into the buffer, transferred to eppendorf tubes and spun to remove debris. Supernatants were boiled for 5 mins, 20 μl aliquots were loaded on a 7% polyaccrylamide gel. Proteins were transferred from the gel to a PVDF membrane (Immobilon, 0.4 μM pore size, Millipore, Bedford, Mass.) with an electro-blotter (Transblot SD, Bio-RAD, Hercules, Calif.). The membrane was blocked in 1% bovine serum albumin (BSA) in Wash Buffer (WB: 10 mM Tris [pH 7.5], 100 mM NaC and 0.1% Tween 20) overnight at 4° C. incubated with mouse anti-iNOS (1:500) IgG2a monoclonal, (Transduction laboratories), diluted in 1% BSA in WB, for 1 hr at room temperature, and washed with WB over 30 minutes. The secondary antibody, anti-mouse IgG (1:3000) horseradish peroxidase conjugate (Bio-RAD), diluted in 5% dry milk in WB was incubated with agitation for 1 hr at room temperature. The membrane was thoroughly washed over 1 hr with WB at room temp and developed with ECL western blotting detection reagents (Amersham, Arlington Heights, Ill.) and exposed to film (X-OMAT AR, Eastman Kodak, Rochester, N.Y.).

Example 1: Reverse Transcriptase PCR

To examine expression of NOS in LC, RNA was extracted from freshly purified murine LC and subjected to RT-PCR with degenerate primers across iNOS, ecNOS and ncNOS. A band of approximately 400 bp was amplified which was more apparent in LPS treated as compared to non-treated cells. To identify the type of NOS, the nucleotide sequence of the PCR product was determined, and found to be identical to mouse macrophage-iNOS.

Primers specific for mouse-iNOS were then used to exclude the possibility that the message obtained above was obtained from contaminating keratinocytes, or other cells. In these experiments, RNA from the LC line XS-52 was subjected to PCR and a specific product was amplified. Based on the following, this band is that of iNOS: First, the length of the band is about 370 nucleotides, second, the band is absent from cells not exposed to LPS and third, no products were seen in the ncNOS-specific primer lanes. Compared to the GAPDH standardized band intensities, it appears that transcription of the RNA in question is LPS dependent. As mentioned above, a faint band is seen in "purified" LC not exposed to LPS lane whereas it is not seen in the XS-52 cells.

Example 2: Anti-iNOS Immunoflourescence

Immunoflourescence with FITC-conjugated anti-iNOS monoclonal antibody of LPS stimulated XS-52 cells showed marked staining compared to that of cells incubated in LPS-free medium. The staining is cytoplasmic sparing the nucleus, and appears granular in some cells. This result suggests that LC express iNOS which is inducible by LPS. Staining of purified LC from BALC/c epidermal cell suspensions was not feasible as the magnetic microspheres used for LC isolation preferentially pick up flourescein, even at maximal dilutions of the antibody.

Example 3: XS-52 Cells Produce NO In Vitro

Supernatants from XS-52 cultures were assayed for the presence of nitrite using the Griess reaction. Those from cells incubated in the presence of LPS showed a dramatic increase in nitrite concentration, reflecting the increase in NO production. In contrast, cells which were not stimulated with LPS produced little NO (FIG. 1A).

To estimate the time required for iNOS induction and subsequent NO production, XS-52 cells were cultured and assayed after various timepoints. Supernatants were assayed from individual wells at each time point to prevent alteration in nitrite concentration due to sampling. A small increase in nitrite levels is seen after 8 hrs but significant levels are obtained after 16 hrs (FIG. 1B).

Purified LC preparations were also assayed for nitrite levels after incubation in LPS. Though elevated nitrite levels are seen in these cells, the results are difficult to reproduce. Nitrite levels are not as high as those with XS-52 cells, probably as these cells go through a difficult purification process, have magnetic spheres adhering to their surface and are fewer in number. Their response to LPS may thus not be optimal.

Example 4: Suppression Of NO Production By L-NAME

To confirm in vitro NO production as seen in the previous experiment, nitrite levels were measured in the presence of LPS and the levorotatory/dextrorotatory, methylated derivatives of L-arginine competitive inhibitors of iNOS. Two such compounds, $N_w$-nitro-L-arginine methyl ester (L-NAME) and $N_w$-nitro-D-arginine methyl ester (D-NAME) were used. Nitrite levels in the presence of LPS were used as control levels of NO production by XS-52 cells. L-NAME inhibited NO production significantly in the presence of LPS, whereas D-NAME did not (FIG. 2). This confirms that LPS-induced NO production in XS-52 cells can be inhibited specifically by the L-methylated forms of L-arginine.

Example 5: Suppression of NO Production by IL-10.

The cytokine IL-10, implicated in a variety of immunomodulatory phenomena, has been shown to affect LC antigen presentation. IL-10 has also been observed to inhibit NOS induction by LPS in macrophages. The previous experiments address inhibition of NOS action only, whereas IL-10 inhibits induction of iNOS. XS-52 cells co-cultured with IL-10 and LPS reproducibly demonstrated inhibition of nitrite production (15–20%) in supernatants (FIG. 3).

Example 6: Effects of LPS, IL-10, and L-NAME on iNOS Expression.

A western blot was done to characterize iNOS levels in cells treated with IL-10 and L-NAME in the presence of LPS. Both L-NAME and IL-10 inhibit NO production (as above), though their mechanism of action is different. Lower levels of iNOS were seen in cells treated with IL-10, (FIG. 4), whereas L-NAME did not affect iNOS expression. Thus, IL-10 inhibits iNOS expression in XS-2 cells whereas L-AME competes with Larginine for the enzyme active site.

It has been shown that LC purified from murine epidermis and XS-2 cells express iNOS and produce NO in response to LPS. RNA isolated from purified LC was initially tested with degenerate primers because it was neither possible to judge whether LC would express NOS at all nor what the isoform would be, iNOS, ecNOS or ncNOS. A dilemma with purifying LC from an epidermal cell suspension is the likelihood of contamination from other sources, leading to erroneous results with PCR. Therefore, once a product was seen at the expected size on electrophoresis, and sequencing data was available, identifying iNOS, a more specific PCR reaction was used, confirming the presence of iNOS mRNA, as seen with macrophages (Denis M. (1994) *J Leuk Biol* 55:682–84). RNA was then isolated from the XS-52 cell line to avoid the potential for contamination and iNOS-specific primers revealed amplification of a specific product, confirming the expression of iNOS in these cells. Such expression was LPS dependent, as in macrophages. In the absence of LPS, amplification of iNOS from LC purified from murine epidermis revealed a faint band not detected in XS-2 cells. This result indicates that in cultured cells, LPS is needed to stimulate iNOS transcription. However, in LC isolated from a 'recently living' mouse exposed to the environment, some LC may have been activated in vivo or during isolation, causing iNOS transcription which may be the cause for the faint band seen. This result indicates a functional role of NO in LC.

These findings were further confirmed by the almost negligible intensity of immunoflourescence seen with XS-2 cells cultured in the absence of LPS. In contrast, LPS stimulation of this cell line resulted in staining with anti-NOS, revealing an increase in quantity of the translated protein. The staining was cytoplasmic, sometimes granular and occasionally dendritic processes stained strongly. The minimal staining seen in the absence of LPS indicates that a small amount of iNOS may be present constitutively, while LPS dramatically increases staining. The exact location of iNOS in the cytoplasm is not known; it may be found in granules or vesicles, either specific to NOS (e.g. nitrovesicles) or non-specific, or it may be found as a free protein. It will be interesting to examine whether iNOS is relocated between granules and cytoplasm after LPS stimulation in these cells.

The results depicted in FIG. 1 demonstrate the induction ol iNOS over time.

These data reveal that finctional iNOS is made, and is capable of producing NO in vitro Allowing 6 hrs for transcription and subsequently translation, LC can respond to stimuli by producing NO within 16 hrs. Isolated LC also can be induced to produce NO after an overnight incubation with LPS. These findings present a number of exciting scenarios as iNOS can produce massive quantities of NO when induced, unlike ncNOS and ecNOS, which are constitutively expressed at a defined level. Toxic and tumorigenic effects of NO are seen at such higher levels of induction(Klostergaard J. (1993) *Res Immunol* 144(4):274–76; Cui et al. (1994) *Cancer Res* 56:2462–67; Ohshima et al. (1994) *Mutation Res* 305:253–64). As LC express iNOS and may be the only cell type in the epidermis doing so, NO produced in LC may be the most abundant form of NOS in the skin, at least in certain conditions i.e. presence of endotoxin.

The fact that NO production in LC can be blocked by using analogues of L-arginine(Moncada et al. (1993) *New Eng J Med* 329:2002–12) (FIG. 2) has important implications for cutaneous pathophysiology. Topical L-AME (1%) has been shown to 30 relieve symptoms and signs of atopic dermatitis(Morita et al. (1994) *Internat J Dermatol* 34:294). Its mechanism of action in that regard is be due to inhibition of LC NO production.

The immunomodulator IL-10 consistently suppresses NO production in XS-52 cells although to a small extent, as in macrophages. IL-10 inhibits antigen presentation through inhibition of B7(Chang et al. (1995) *Eur J Immunol* 25:394–398), a costimulatory molecule, expressed with MHC-I. A decrease in NO production secondary to IL-10 may mean that NO partly mediates the effects of IL-10. Also, IL-10 treated cells showed lower levels of iNOS as opposed to cells treated with L-NAME, though both substances inhibit NO production.

Example 7: Nitric Oxide is Toxicfor Melanocytes

Melanocyte susceptibility to NO was examined using NO donor compounds and NO released by a Langerhans cell-like cell line.

Sodium nitroprusside (SNP) is a donor of NO in aqueous solution. Melanocyte lysis was seen in the presence of 0.01–1 mM SNP over 24 hrs, quantified by chromium release. Chromium release was seen to be both time- and SNP dose-dependent, with more chromium being released from melanocytes at a higher SNP-concentration and longer time course. Maximum chromium release of up to 80–90% was seen at 16 hrs after addition of 1 mM SNP.

Langerhans cells (LC) express inducible NOS and produce large amounts of NO. Because LC lie in close proximity to melanocytes in the epidermis, it was hypothesized that the large amounts of NO produced by LC may affect melanocyte function and survival, resulting in pathological manifestations. Co-culture of an LC-like cell line (XS cells) with melanocytes followed by the induction of iNOS by LPS resulted in melanocyte cell death. As melanocytes do not express iNOS, LPS had no effect on melanocytes stimulated with LPS in the absence of XS cells. Melanocyte lysis was also seen when cocultures were performed across Transwells®, with no direct cell-cell contact between XS cells and melanocytes. Thus LC-induced melanocyte death was dependent on a diffusible factor consistent with NO. To confirm that this substance was indeed NO, cocultures were performed in L-arginine deficient media (reversible by addition of L-arginine) or in the presence of NO quencher, reduced hemoglobin. Melanocyte toxicity was remarkable reduced under both conditions. These results indicate an NO-dependent interaction between LC and melanocytes. Thus, nitric oxide from LC and NO donors is cytotoxic for melanocytes.

Equivalents

Those skilled in the art will be able to recognize, or be able to ascertain using no more than routine experimentation, numerous equivalents to the specific procedures described herein. Such equivalents are considered to be within the scope of this invention and are covered by the following claims.

What is claimed is:

1. A method of treating a subject for a condition characterized by excess pigmentation comprising: selecting a subject in need of skin lightening; and admistering to the subject a treatment which increases the level of NO in the skin thereby lighting the skin of the subject.

2. A method of treating a subject for a condition characterized by a lack of pigmentation comprising: selecting a subject in need of skin darkening; and administering to the subject, a treatment which reduces the level of NO in the skin, thereby lightening the skin of the subject.

3. The method of claim 2, wherein said condition is: vitiligo; post-inflammatory hypopigmentation; or idiopathic guttate hypomelanosis (IGH).

4. The method of claim 2, wherein the treatment includes the administration of a compound which inhibits the level of NO in the skin of the subject.

5. The method of claim 4, wherein the treatment includes the administration of an inhibitor of NO synthase or an NO scavenger.

6. The method of claim 1, wherein the treatment includes the administration of a compound which increases the level of NO in the skin of the subject.

7. The method of claim 6, wherein the treatment includes the administration of an NO donor compound.

8. The method of claim 1, wherein the condition is post-inflammatory hyperpigmentation.

* * * * *